United States Patent [19]

Bolton et al.

[11] 3,939,154

[45] Feb. 17, 1976

[54] PYRAZOLINE DERIVATIVES

[75] Inventors: Ivan Joseph Bolton, Bingley, England; Fritz Fleck, Bottmingen, Switzerland; Alec Victor Mercer, Leeds, England

[73] Assignee: Sandoz Ltd., (Sandoz AG), Basle, Switzerland

[22] Filed: Jan. 24, 1974

[21] Appl. No.: 436,129

[30] Foreign Application Priority Data

Jan. 29, 1973 United Kingdom ................ 4366/73

[52] U.S. Cl. ............................................ 260/239.9

[51] Int. Cl.² ........................................ C07D 231/06

[58] Field of Search ................................ 260/239.9

[56] References Cited

UNITED STATES PATENTS

| | | | |
|---|---|---|---|
| 3,135,742 | 6/1964 | Wagner et al. | 260/239.9 |
| 3,255,203 | 6/1966 | Shinzel et al. | 260/239.9 |
| 3,406,163 | 10/1968 | Meininger et al. | 260/239.9 |
| 3,574,195 | 4/1971 | Hajek | 260/239.9 |
| 3,630,895 | 12/1971 | Krause et al. | 260/239.9 |

*Primary Examiner*—Sam Rosen
*Attorney, Agent, or Firm*—Gerald D. Sharkin; Richard E. Vila; Thomas C. Doyle

[57] ABSTRACT

The invention relates to optical brightening agents.

62 Claims, No Drawings

PYRAZOLINE DERIVATIVES

The invention relates to optical brightening agents.

According to the invention, there are provided compounds of formula I,

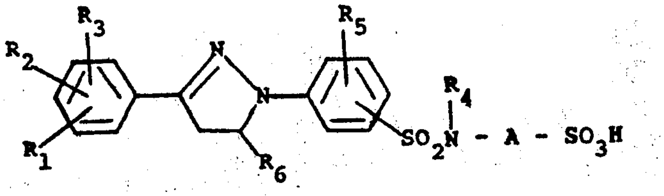

I in which either $R_2$ and $R_3$, which may be the same or different, each signifies a hydrogen atom, a halogen atom, an alkyl radical of 1 to 4 carbon atoms, an alkoxy radical of 1 to 4 carbon atoms, a cyano radical or a sulphonic acid group, and $R_1$ signifies a halogen atom, an alkyl radical of 1 to 4 carbon atoms, an alkoxy radical of 1 to 4 carbon atoms, a cyano radical, a sulphonic acid group or a phenyl radical, or $R_1$ and $R_2$, together, form a methylenedioxy group, $R_3$ being as defined above, $R_4$ signifies a hydrogen atom, or an alkyl radical of 1 to 4 carbon atoms.

$R_5$ signifies a hydrogen atom, a halogen atom, an alkyl radical of 1 to 4 carbon atoms or an alkoxy radical of 1 to 4 carbon atoms, $R_6$ signifies a hydrogen atom, an alkyl radical of 1 to 4 carbon atoms, an unsubstituted phenyl radical or a phenyl radical substituted by a chlorine atom, an alkyl radical of 1 to 4 carbon atoms or a sulphonic acid group, and A signifies a phenylene radical or an alkylene chain of 1 to 4 carbon atoms, unsubstituted or substituted by an alkyl radical of 1 to 4 carbon atoms, which compounds may be in free acid or salt form, and the use thereof in dyeing fibrous substrates, particularly of natural or synthetic polyamide fibres.

$R_4$ signifies a hydrogen atom, or an alkyl radical of 1 to 4 carbon atoms.

$R_5$ signifies a hydrogen atom, a halogen atom, an alkyl radical or 1 to 4 carbon atoms or an alkoxy radical of 1 to 4 carbon atoms, $R_6$ signifies a hydrogen atom, an alkyl radical of 1 to 4 carbon atoms, an unsubstituted phenyl radical or a phenyl radical substituted by a chlorine atom, an alkyl radical of 1 to 4 carbon atoms or a sulphonic acid group, and A signifies a phenylene radical or an alkylene chain of 1 to 4 carbon atoms, unsubstituted or substituted by an alkyl radical of 1 to 4 carbon atoms, which compounds may be in free acid or salt form.

The invention also provides a process for the production of compounds of formula I, characterised by (a) reacting a compound of formula II,

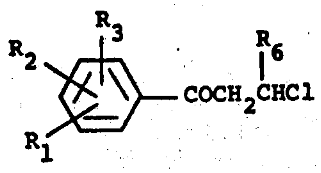

II in which $R_1$, $R_2$, $R_3$ and $R_6$ are as defined above, with a compound of formula III,

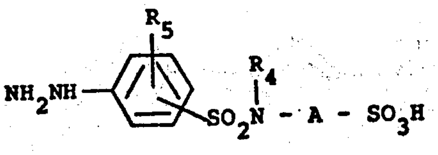

III in which $R_4$ $R_5$ and A are as defined above, (b) reacting a compound of formula IV,

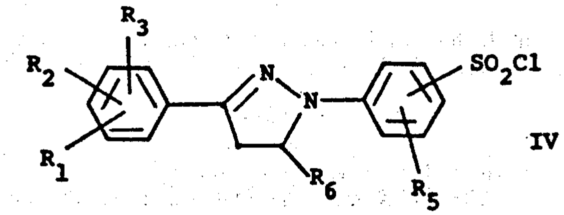

IV in which $R_1$, $R_2$, $R_3$, $R_5$ and $R_6$ are as defined above, with a compound of formula V, $R_4NHASO_3H$ in which $R_4$ and A are as defined sbove, (c) reacting a compound of formula VI,

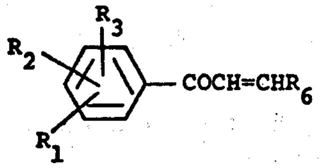

VI in which $R_1$, $R_2$, $R_3$ and $R_6$ are as defined above, with a compound of formula III, stated above, (d) obtaining a compound of formula Ia,

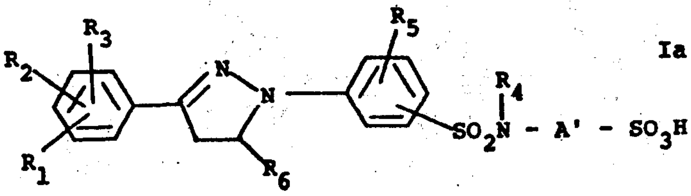

Ia in which $R_1$, $R_2$, $R_3$, $R_4$, $R_5$ and $R_6$ are as defined above, and A' signifies

in which $R_7$ signifies a hydrogen atom, or an alkyl radical of 1 to 4 carbon atoms.

by reacting a compound of formula VII,

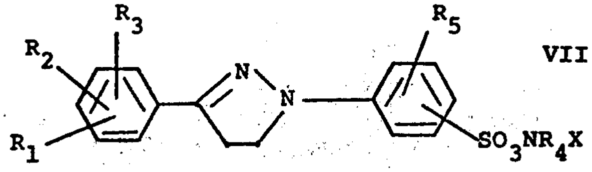

VII in which $R_1$, $R_2$, $R_3$ $R_4$ are as defined above, with a compound of formula VIII, $MX'SO_3$ VIII in which M signifies an alkali metal, and a compound of formula IX, $R_7CHO$ IX in which $R_7$ is as defined above, and one of X and X' signifies a hydrogen atom, the other signifies an alkali metal, (e) obtaining a compound of formula Ib,

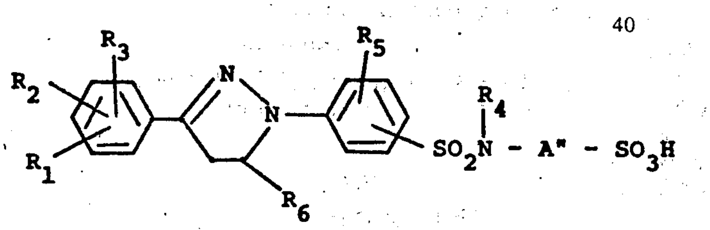

Ib in which $R_1$, $R_2$, $R_3$, $R_4$, $R_5$ and $R_6$ are as defined above, and A'' signifies an alkylene chain of 3 chain carbon atoms, which is unsubstituted or substituted by an alkyl radical of 1 to 4 carbon atoms, by reacting a compound of formula X,

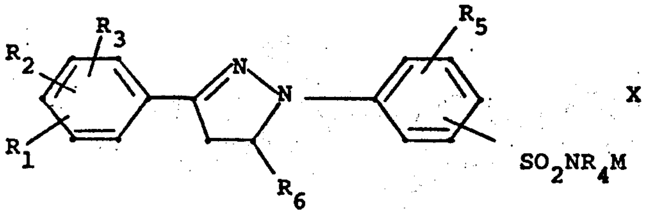

X in which $R_1$, $R_2$, $R_3$, $R_4$, $R_5$, $R_6$ and M are as defined above, with a compound of formula XI,

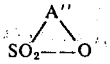

XI in which A'' is as defined above, or (f) obtaining a compound of formula Ic,

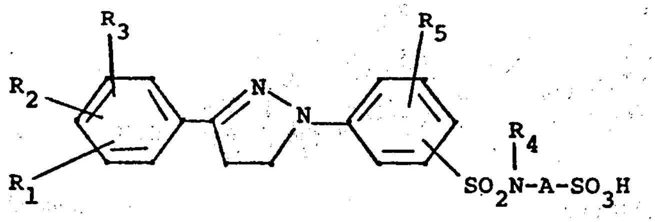

Ic in which $R_1$, $R_2$, $R_3$, $R_4$, $R_5$ and A are as defined above, by reacting a compound of formula XII

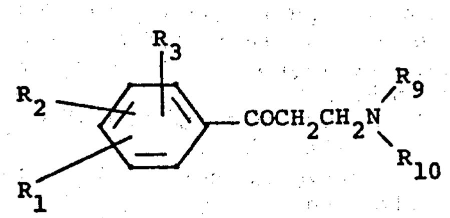

XII in which $R_1$, $R_2$ and $R_3$ are as defined above, and either $R_9$ and $R_{10}$, which may be the same or different, each signifies a hydrogen atom or an alkyl radical of 1 to 6 carbon atoms, or $R_9$ and $R_{10}$ are joined to form, together with the nitrogen atom to which they are attached, a heterocyclic ring which optionally contains a further hetero atom to the nitrogen atom, with a compound of formula III, stated above.

In the above process, the reagents involved, which are shown to be in free acid form, e.g. compounds of formulae III and V may, of course, be in salt form.

Process (a) is conveniently carried out by reacting the compounds of formula II with the compound of formula III in water, a water-miscible solvent or a mixture thereof. A suitable reaction temperature is from 20° to 200°C, preferably at 70° to 110°C. A suitable reaction time is from 1 to 12 hours. Suitable solvents include methanol, ethanol, isopropanol, cellosolve, acetic acid, dimethyl formamide, dioxan or pyridine.

Process (b) is conveniently carried out by adding the compound of formula IV, in a water-miscible solvent, to the compound of formula V and carrying out the reaction in the solvent or in a mixture of the solvent and water. The solvent may, for example, be dimethylformamide, dioxan or pyridine. A suitable reaction time is from 1 to 12 hours. The reaction is preferably carried out at a temperature of from 0° to 50°C, preferably 20° to 30°C and preferably at a pH of from 5 to 9.

Process (c) is conveniently carried out by reacting the compounds of formula VI with the compound of formula III in a water-miscible organic solvent. A suitable reaction temperature is from 20° to 150°C, preferably from 60° to 110°C. As Examples of solvents may be given methanol, ethanol, isopropanol, cellosolve and dioxan. The reaction time is conveniently from 1 to 12 hours. The reaction is preferably carried out at a pH of from 1 to 3.

Process (d) is conveniently carried out by reacting the compounds of formulae VII, VIII and IX in water, a water-miscible solvent or a mixture thereof. A suitable reaction temperature is from 20° to 150°C, preferably from 80° to 110°C. As examples of solvents may be given methanol, ethanol, isopropanol, cellosolve, dimethylformamide and dioxan. A suitable reaction time is from 1/2 to 5 hours.

Process (e) is conveniently carried out by reacting the compounds of formulae X and XI, either alone or in a solvent. A suitable reaction temperature is from 60° to 150°C, preferably from 80° to 110°C. As examples of solvents may be given acetone, dioxan and toluene. A suitable reaction time is from 1 to 16 hours.

Process (f) is conveniently carried out by reacting the compounds of formulae XII and III in a water-miscible solvent, with or without addition of water, at a temperature of from 20° to 200°C, preferably from 60° to 110°C. As examples of solvents may be given methanol, ethanol, isopropanol, cellosolve and dioxan. A suitable reaction time is from 1 to 12 hours. The reaction is preferably carried out at a pH of from 7 to 9.

The resulting compounds of formula I may be isolated and purified using conventional techniques.

The preferred salt forms of the compounds of formula I are the alkali metal and ammonium salt forms, the sodium salt form being most preferred.

As examples of other salt forms may be given the salts formed with cations of formula $R_{11}R_{12}R_{13}N^+H$, in which $R_{11}$, $R_{12}$ and $R_{13}$, independently, signify hydrogen or an alkyl radical of 1 to 4 carbon atoms, unsubstituted or substituted by 1 to 2, preferably 1, hydroxy group, at least one of $R_{11}$, $R_{12}$ and $R_{13}$ signifying other than hydrogen. As examples may be given the mono-, di- and tri-ethanolamine and mono-, di- and tri-isopropanolamine salt forms. The salt forms are obtained in conventional manner from the free acid forms and vice versa and, as will be appreciated, the salt forms are interconvertible in known manner.

In the compounds of formula I, any alkyl or alkoxy radical may, for example, be a methyl, ethyl, isopropyl, tert-butyl or methoxy, ethoxy, isopropoxy or tert-butoxy radical, the preferred such radicals being methyl, ethyl, methoxy or ethoxy. Any halogen atom may be chlorine, bromine, or fluorine, chlorine and fluorine being preferred, chlorine most preferred.

The preferred compounds of formula I are those of formula I',

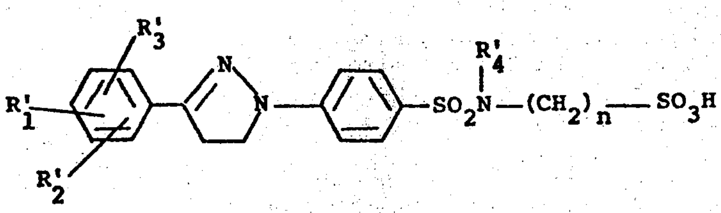

I' in which $R_2'$ and $R_3'$, which may be the same or different, each signify a hydrogen atom, a chlorine atom or a methyl radical, $R'_1$ signifies a chlorine atom or a methyl radical, $R'_4$ signifies a hydrogen atom or a methyl radical, and

*n* signifies 1, 2 or 3, which compounds are in free acid or salt form.

In the preferred compounds of formula I', the 4-position of the 3-phenyl radical is unsubstituted or substituted by chlorine.

Still more preferred compounds of formula I are those of formula I'',

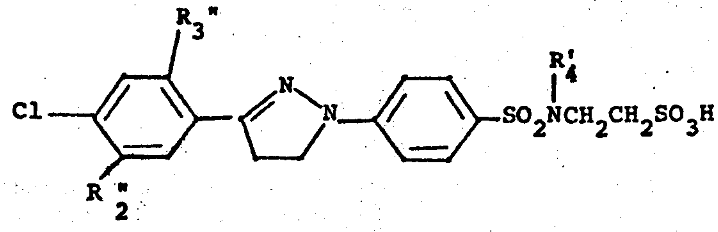

I'' in which either $R''_2$ and $R''_3$ both signify hydrogen atoms, or $R''_2$ signifies a chlorine atom, and $R_3''$ signifies a methyl radical, and $R_4'$ is as defined above, which compounds are in free acid or salt form.

The compounds of formula I are useful as optical brightening agents, giving good results on natural or synthetic polyamide fibres, particularly on nylon 6 or nylon 6,6 fibres. Thus the invention also provides a process for optically brightening a fibrous substrate, preferably of natural or synthetic polyamide fibres, particularly nylon 6 or nylon 6,6 fibres, comprising applying thereto, as brightening agent, a compound of formula I.

The compounds of formula I may be applied to the polyamide fibres, which may be, for example, in yarn, non-woven, woven or knitted form, in conventional manner, for example by the so-called "thermosol"

application method, (Gunn and Nightingale "Cotton and Man-Made Fibres Year Book" 1966–67, p. 410).

In such process the compounds are applied in amount of from 0.01% to 0.7%, preferably 0.05% to 0.3% based on the weight of substrate. The substrate is padded with liquor at a temperature of from 0° to 60°C, preferably 10° to 50°C at a pick-up of from 20 to 120%, preferably 40 to 90%, the liquor containing such additives as surfactants and formic acid etc. as desired. The subsequent heat treatment applied for 5 to 120 secs, preferably 15 to 60 secs, the temperature being 140° to 190°C, preferably 160° to 185°C, for nylon 6 and 140° to 220°C, preferably 170° to 200°C for nylon 6,6.

The compounds give notably bright effects when applied by this method. Other methods include the so-called "acid flash" procedure and exhaust, acid or neutral bath, methods.

The following Examples, in which all parts and percentages are by weight and all temperatures are in degrees centigrade, illustrate the invention.

EXAMPLE I 28.0 g of p-(β-sulphoethylsulphonamido) aniline was slurried in a mixture of 30 ml of water and 30 ml concentrated hydrochloric acid (d = 1.18) at 5°. A solution of 7.6 g sodium nitrite in 20 ml water was added to the well stirred solution over 5 minutes at 5°–10° and the resulting suspension stirred for a further half hour. The diazonium slurry was added in poritions at 0°–5° to a well stirred solution of 31.5 g of sodium sulphite and 20.0 g of sodium carbonate in 60 ml of water. The resulting solution was stirred at 5° for 1 hour, warmed to 70° over 1 hour, and then treated with 120 ml of concentrated hydrochloric acid. The solution was heated for a further 2 hours at 70° and was then evaporated to dryness to give a crude solid containing 15.0 g p-(β-sulphoethylsulphonamido)phenyl hydrazine.

The crude hyrazine 15.0 g, 10.3 g β-chloroethyl - p-chlorophenyl ketone and 20.0 g sodium acetate were slurried in 50 ml of water and 200 ml glacial acetic acid. The mixture was heated to reflux for one hour, and 150 ml water then added. 20.0 g of sodium chloride was added to the hot solution, which was then cooled to give the pyrazoline

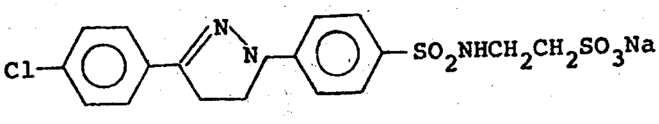

as a pale yellow solid.

A further compound of formula I, prepared in a similar manner and in which $R_4$ is hydrogen and the aminosulphonyl group is in *p* position, is shown in the following table.

| Ex. | A | $R_5$ | $R_6$ | $R_1$ and posn. | $R_2$ and posn. | $R_3$ and posn. | Appearance |
|---|---|---|---|---|---|---|---|
| 2 | $-CH_2-CH_2-$ | H | H | 3'-Cl | 4'-Cl | 6'-$CH_3$ | Pale yellow solid |

EXAMPLE 3

33.55 g of 1-(p-Sulphonamido phenyl)-3-(p-chlorophenyl)-$\Delta^2$-pyrazoline in 200 ml cellosolve was stirred and refluxed while a solution of 4.8 g sodium hydroxide in 10 ml of water was added dropwise. The resulting slurry was cooled to 10°, filtered, and washed with 50 ml of ethanol. The wet cake was dissolved in a mixture of 200 ml of water and 400 ml dimethylformamide, and treated at 25° with a solution of sodium metabisulphite (55.5 g) and formaldehyde (40 ml of 40% aqueous solution) in 250 ml of water. The mixture was heated to reflux over ½ hour, refluxed for one hour, then allowed to cool slowly to give the pyrazoline

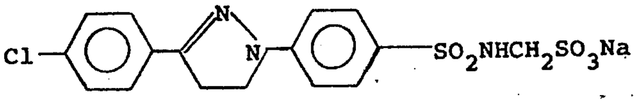

as a pale yellow solid.

By repeating the procedure of Example 3, but using appropriate starting materials, the compounds shown in the following Table may be obtained.

| Example | Compound | Appearance |
|---|---|---|
| 3a | 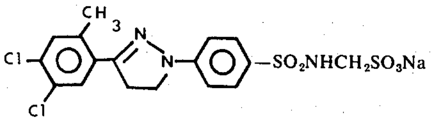 | Pale yellow solid |
| 3b | 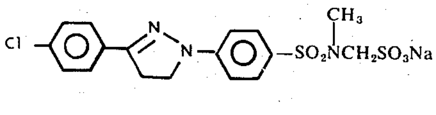 | Pale yellow solid |
| 3c | 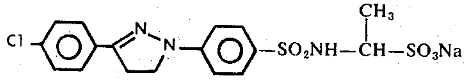 | Pale yellow solid |

EXAMPLE 4

A slurry of 46.7 g p-acetamidobenzene sulphonyl chloride and 35.4 g N-methyl taurine sodium salt in 400 ml water was stirred at 20°–25°C. The pH of the slurry was maintained at 7–8 by the addition of 16.8 g sodium bicarbonate in portions over 1 hour. The resulting solution was treated with 100 ml concentrated hydrochloric acid ($d$ = 1.18) and was then heated to reflux for 10 minutes. The solution was cooled to 5°C and a solution of 14.0 g sodium nitrite in 40 ml water was added at 5°–10°C over 10 minutes. The resulting solution was stirred for a further 20 minutes, and was then added in portions at 0°–5°C to a well stirred solution of 63.0 g sodium sulphite and 40.0 g sodium carbonate in 120 ml water. The solution was stirred at 5°C for 1 hour, warmed to 70°C over 1 hour, and then treated with 300 ml concentrated hydrochloric acid. The solution was heated for a further 2 hours at 70°C and was then cooled to 0°C and filtered to give a crude solid containing 46.4 g p-[N-methyl-N-(β-sulphoethyl) sulphonamido] phenyl hydrazine.

The crude hydrazine (46.4 g), 37.7 g β-chloroethyl(2-methyl-4,5-dichloro)phenyl ketone, and 50.0 g sodium acetate were slurried in 100 ml water and 300 ml glacial acetic acid. The mixture was heated to reflux for 1½ hours, and 150 ml water was then added to give a clear solution, which was cooled to 0°C to give the pyrazoline as a pale yellow solid.

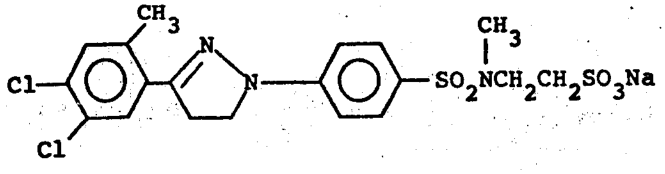

By repeating the procedure of Example 4, but using appropriate starting materials, the following compounds may be obtained.

| Example | Compound | Appearance |
|---|---|---|
| 5 | 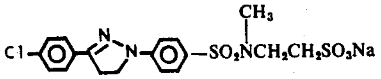 | Pale yellow solid |
| 6 | 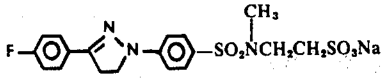 | Pale yellow solid |
| 7 | 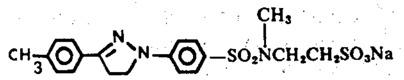 | White solid |
| 8 | 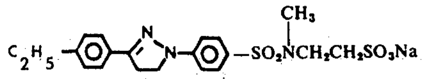 | Pale yellow solid |
| 9 | 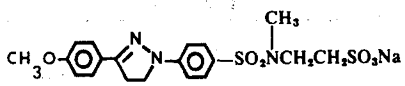 | Pale yellow solid |
| 10 | 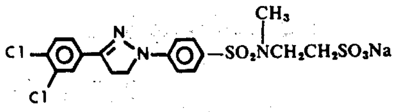 | Yellow solid |
| 11 | 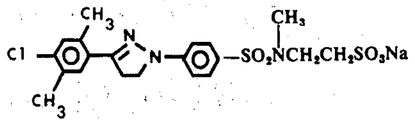 | Pale yellow solid |
| 12 | 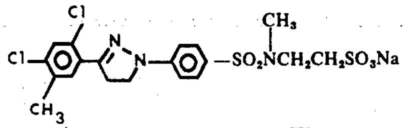 | Yellow solid |
| 13 | 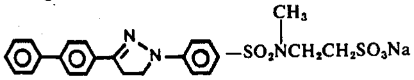 | Yellow solid |
| 14 | 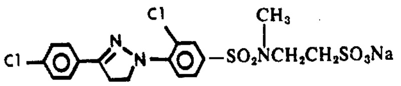 | White solid |
| 15 | 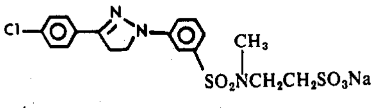 | Pale yellow solid |
| 15a | 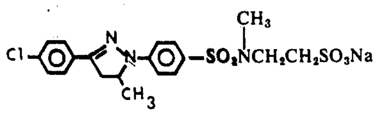 | Pale yellow solid |

EXAMPLE 16

35.5 g of 1-(p-chlorosulphonyl phenyl)-3-(p-chlorophenyl)-$\Delta^2$-pyrazoline was dissolved in 350 ml dimethyl-formamide and the resulting solution was added dropwise at 25°C to a stirred mixture of 32.2 g of N-methyltaurine sodium salt, 35 ml water and 70 ml dimethylformamide. The pH of the mixture was maintained at 7–8 by adding sodium bicarbonate in portions during the addition and whilst the resultant mixture was stirred for a further two hours at 25°C, 350 ml water was added to the mixture, which was then heated to the boil, treated with 70 g of sodium chloride, and cooled slowly with stirring to 10°C to give 36 g of the pyrazoline

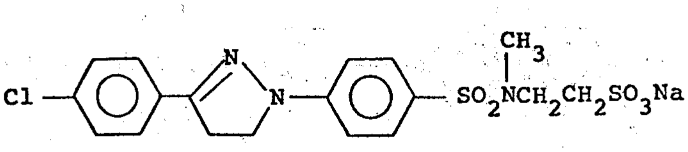

described in Example 5 above.

By repeating the procedure of Example 16, but using appropriate starting materials, the compounds shown in the following Table can be obtained.

| Example | Compound | Appearance |
|---|---|---|
| 17 | 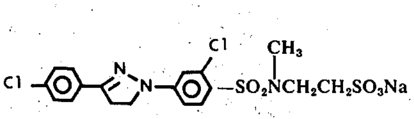 | Pale yellow solid |
| 18 | 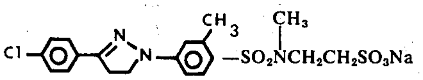 | Pale yellow solid |
| 19 | 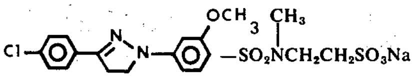 | Pale yellow solid |

EXAMPLE 20

24.3 g of 4'-chlorochalcone and 30.9 g of p-[N-methyl-N-($\beta$-sulphoethyl) sulphonamido] phenyl hydrazine sodium salt were slurried together in 200 ml ethanol and the pH was adjusted to 1–2 with concentrated hydrochloric acid. A further 10 ml concentrated hydrochloric acid was added and the mixture was heated to the boil and stirred under reflux for four hours. 100 ml Water was added to the hot mixture, the pH was adjusted to 4–5 with sodium hydroxide solution, and the solution was cooled slowly with stirring to 10°C to give 49.5 g of the pyrazoline

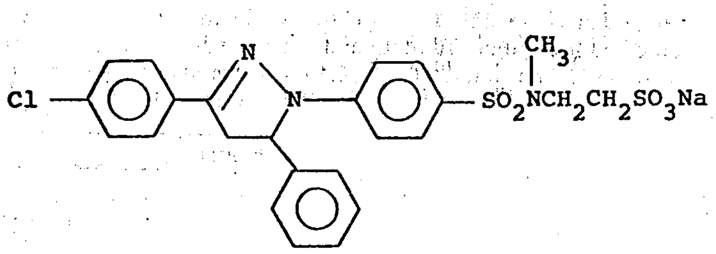

as a pale yellow solid.

By repeating the procedure of Example 20, but using appropriate starting materials, the compounds in the following table may be obtained.

| Example | Compound | Appearance |
|---|---|---|
| 20a | 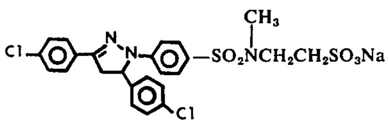 | yellow solid |
| 20b | 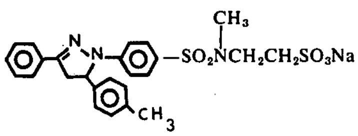 | pale yellow solid |
| 20c | 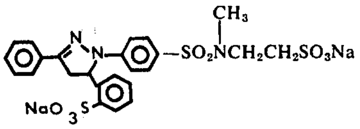 | pale yellow solid |

EXAMPLE 21

33.5 g of 1-(p-sulphonamido phenyl)-3-(p-chlorophenyl)-$\Delta^2$-pyrazoline in 200 ml cellosolve was stirred and heated under reflux while a solution of 4.8 g sodium hydroxide in 10 ml water was added dropwise. The resulting slurry was cooled to 10°C, filtered, and washed with 50 ml acetone. The wet cake was slurried in 450 ml acetone, 13.4 g of propane sultone was added, and the mixture was heated to the boil and stirred under reflux for 16 hours. 50 ml of water was added and the mixture was cooled to 10°C and filtered to give the pyrazoline

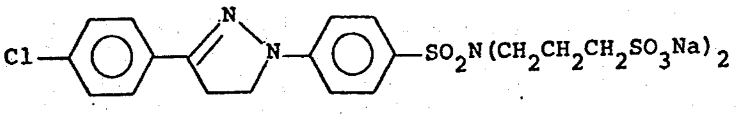

as an off white solid.

The filtrates were evaporated to dryness and the resultant residue was slurried with 200 ml acetone and filtered to give the pyrazoline

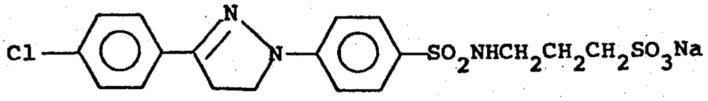

as a pale yellow solid.

EXAMPLE 22

27.1 g of 2-methyl-4,5-dichloroacetophenone, 18.1 g of morpholine hydrochloride and 4.4 g of paraformaldehyde were slurried in 60 ml cellosolve. The mixture was heated to the boil, stirred under reflux for 1 hour, cooled to 0°C, and filtered. The resultant wet cake was slurried in 200 ml cellosolve with 30.9 g of p-[N-methyl-N-($\beta$-sulphoethyl) sulphonamido] phenyl hydrazine and 20 g of sodium carbonate. The mixture was heated to the boil and stirred under reflux for 16 hours. 200 ml Water was added, the pH was adjusted to 4–5 with hydrochloric acid, and the solution was cooled to 10°C and filtered to give 39 g of the pyrazoline

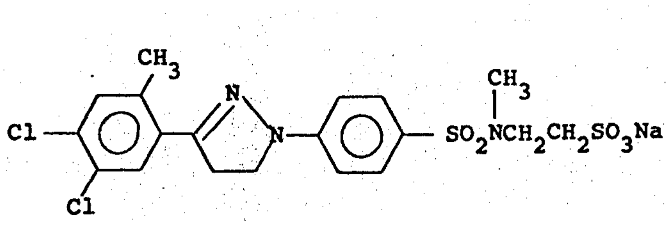

described in Example 4 above.

By repeating the procedure of Example 22, but using appropriate starting materials, the compounds shown in the following Table can be obtained.

| Example | Compound | Appearance |
|---|---|---|
| 23 | 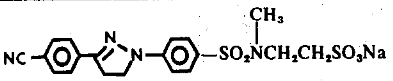 | Yellow solid |
| 24 | 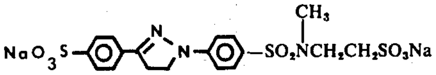 | Yellow solid |
| 25 | 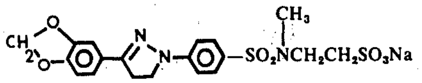 | Pale yellow solid |
| 26 | 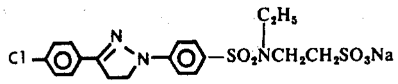 | Pale yellow solid |
| 27 | 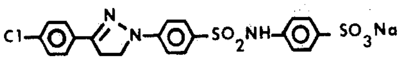 | Pale yellow solid |
| 28 | 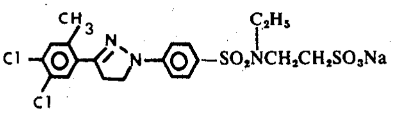 | Pale yellow solid |
| 29 | 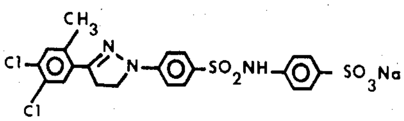 | Pale yellow solid |

APPLICATION EXAMPLE A

A strip of white nylon 6.6, 15 cms wide and weighing 8 gms, was padded at 100% expression through a solution containing 0.2% of the pyrazoline produced in Example 1, 2% of a non-ionic alkylene oxide adduct of an alkylated phenol and 0.2% formic acid. The nylon piece was dried at 80°C and then passed through an oven at 180° for 30 seconds. The treated piece showed a brilliant whiteness compared with the untreated piece.

APPLICATION EXAMPLE B

A strip of white nylon 6.6 was treated by the method described in Example A except that the pyrazoline produced in Example 2 was used as the brightening agent. The treated piece showed a brilliant whiteness compared with the untreated piece.

APPLICATION EXAMPLE C

A 5 gm piece of bleached wool was treated with 200 mls of a solution containing 10 milligrams of the pyrazoline produced in Example 1 and 1 gram of a bleaching agent based on sodium hydrosulphite. The piece was entered at 40°, the temperature of the bath raised to 70° over 15 minutes and maintained at 70° for a further 30 minutes. 1.5 ml of a 10% solution of acetic acid was then added to the bath and the treatment continued at 70° for a further 15 minutes. The piece was then removed from the bath, rinsed in cold demineralized water and dried in an oven at 80°. The treated piece showed a distinct whiteness compared to the untreated material.

APPLICATION EXAMPLE D

A 5 gm piece of white nylon 6.6 was treated with 200 ml of a solution containing 10 milligrams of the pyrazoline produced in Example 1 and 150 mg of acetic acid. The piece was entered at 40°, the temperature of the bath increased to 90°–100° over 30 minutes and then maintained at 90°–100° for a further 30 minutes. The piece was removed from the bath, rinsed in cold demineralized water and dried in an oven at 80°. The treated piece showed a brilliant whiteness compared to the untreated material.

APPLICATION EXAMPLE E

A strip of nylon 6,6, 15 cm wide and weighing 8 gm, was padded at 100% expression through a solution containing 0.2% of the pyrazoline produced in Example 4. The nylon piece was boiled for 1 minute in 240 ml of water containing 0.2% acetic acid, and was then washed off in boiling water for 1 minute. The piece was then rinsed in cold demineralised water and dried in an oven at 80°C. The treated piece showed a brilliant whiteness compared to the untreated piece.

APPLICATION EXAMPLE F

A strip of white nylon 6 was treated by the method described in Example A except that the pyrazoline produced in Example 4 was used as the brightening agent. The treated piece showed a brilliant whiteness compared with the untreated piece.

What is claimed is:

1. A compound of formula I,

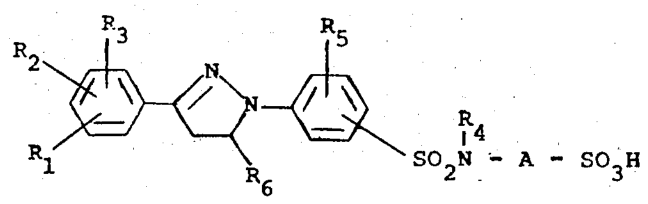

in which $R_1$ is halogen or alkyl of 1 to 4 carbon atoms,
  $R_2$ and $R_3$, which may be the same or different, are hydrogen, halogen or alkyl of 1 to 4 carbon atoms,
  $R_4$ is hydrogen or alkyl of 1 to 4 carbon atoms,
  $R_5$ signifies a hydrogen atom, a halogen atom, an alkyl radical of 1 to 4 carbon atoms or an alkoxy radical of 1 to 4 carbon atoms,
  $R_6$ is hydrogen or alkyl of 1 to 4 carbon atoms, and
  A is an alkylene chain of 1 to 3 carbon atoms,
which compound is in free acid or salt form.

2. A compound of claim 1, wherein $R_1$ signifies a halogen atom.

3. A compound of claim 2, wherein either $R_2$ and $R_3$ both signify hydrogen or one signifies a halogen atom, the other an alkyl radical of 1 to 4 carbon atoms.

4. A compound of claim 3, wherein $R_2$ and $R_3$ both signify hydrogen.

5. A compound of claim 4, wherein $R_1$ is located on the 4-position of the ring to which it is attached.

6. A compound of claim 3, wherein $R_2$ signifies a halogen atom and $R_3$ signifies an alkyl radical of 1 to 4 carbon atoms.

7. A compound of claim 6, wherein $R_3$ is located at the 2 position of the ring to which it is attached and $R_2$ to the 5 position.

8. A compound of claim 7, wherein $R_1$ is located at the 4-position of the ring to which it is attached.

9. A compound of claim 5, wherein the halogen is chlorine.

10. A compound of claim 8, wherein the halogen is chlorine and the alkyl radical of 1 to 4 carbon atoms is methyl.

11. A compound of claim 2, wherein A signifies an alkylene chain of 1 to 3 carbon atoms.

12. A compound of claim 3, wherein A signifies an alkylene chain of 1 to 3 carbon atoms.

13. A compound of claim 5, wherein A signifies an alkylene chain of 1 to 3 carbon atoms.

14. A compound of claim 9, wherein A signifies an alkylene chain of 1 to 3 carbon atoms.

15. A compound of claim 10, wherein A signifies an alkylene chain of 1 to 3 carbon atoms.

16. A compound of claim 1, wherein A signifies an alkylene chain of 1 or 3 carbon atoms.

17. A compound of claim 1, wherein A signifies an alkylene chain of 2 carbon atoms.

18. A compound of claim 11, wherein A signifies an alkylene chain of 1 or 3 carbon atoms.

19. A compound of claim 11, wherein A signifies an alkylene chain of 2 carbon atoms.

20. A compound of claim 12, wherein A signifies an alkylene chain of 1 or 3 carbon atoms.

21. A compound of claim 12, wherein A signifies an alkylene chain of 2 carbon atoms.

22. A compound of claim 13, wherein A signifies an alkylene chain of 1 or 3 carbon atoms.

23. A compound of claim 13, wherein A signifies an alkylene chain of 2 carbon atoms.

24. A compound of claim 14, wherein A signifies an alkylene chain of 1 or 3 carbon atoms.

25. A compound of claim 14, wherein A signifies an alkylene chain of 2 carbon atoms.

26. A compound of claim 15, wherein A signifies an alkylene chain of 1 or 3 carbon atoms.

27. A compound of claim 15, wherein A signifies an alkylene chain of 2 carbon atoms.

28. A compound of claim 1, wherein $R_4$ signifies a hydrogen atom.

29. A compound of claim 1, wherein $R_4$ signifies an alkyl radical of 1 to 4 carbon atoms.

30. A compound of claim 4, wherein $R_4$ signifies a hydrogen atom.

31. A compound of claim 4, wherein $R_4$ signifies an alkyl radical of 1 to 4 carbon atoms.

32. A compound of claim 16, wherein $R_4$ signifies a hydrogen atom.

33. A compound of claim 16, wherein $R_4$ signifies a $C_{1-4}$ alkyl group.

34. A compound of claim 17, wherein $R_4$ signifies a hydrogen atom.

35. A compound of claim 17, wherein $R_4$ signifies a $C_{1-4}$ alkyl group.

36. A compound of claim 1, wherein $R_6$ signifies a hydrogen atom.

37. A compound of claim 1, wherein $R_6$ signifies a $C_{1-4}$ alkyl radical.

38. A compound of claim 1, of formula I'

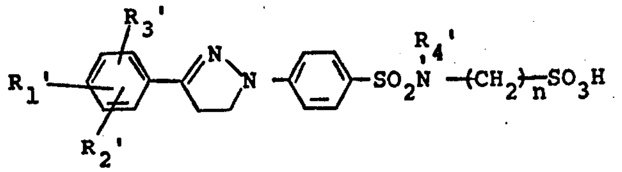

I' in which $R_2'$ and $R_3'$, which may be the same or different, each signify a hydrogen atom, a chlorine atom or a methyl radical, $R_1'$ signifies a chlorine atom or a methyl radical,
$R_4'$ signifies a hydrogen atom or a methyl radical, and
$n$ signifies 1, 2 or 3, which compound is in free acid or salt form.

39. A compound of claim 38, wherein $R_2'$ and $R_3'$ both signify hydrogen and $R_1'$ signifies chlorine.

40. A compound of claim 38, wherein two of $R_1'$, $R_2'$ and $R_3'$ signify chlorine, the other signifying methyl.

41. A compound of claim 39, wherein $R_4'$ signifies hydrogen.

42. A compound of claim 39, wherein $R_4'$ signifies methyl.

43. A compound of claim 40, wherein $R_4'$ signifies hydrogen.

44. A compound of claim 40, wherein $R_4'$ signifies methyl.

45. A compound of claim 41, wherein $n$ signifies 1 or 3.

46. A compound of claim 41, wherein $n$ signifies 2.

47. A compound of claim 42, wherein $n$ signifies 1 or 3.

48. A compound of claim 42, wherein $n$ signifies 2.

49. A compound of claim 43, wherein $n$ signifies 1 or 3.

50. A compound of claim 43, wherein $n$ signifies 2.

51. A compound of claim 44, wherein $n$ signifies 1 or 3.

52. A compound of claim 44, wherein $n$ signifies 2.

53. A compound of claim 38, and of formula I'',

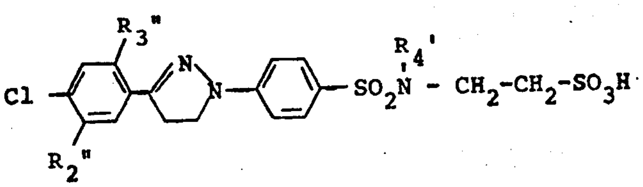

I'' in which either $R_2''$ and $R_3''$ both signify hydrogen atoms, or
$R_2''$ signifies a chlorine atom, and
$R_3''$ signifies a methyl radical, and
$R_4'$ signifies a hydrogen atom or a methyl radical,
which compound is in free acid or salt form.

54. A compound of claim 53, wherein $R_4'$ signifies a methyl radical.

55. A compound of claim 54 of the formula

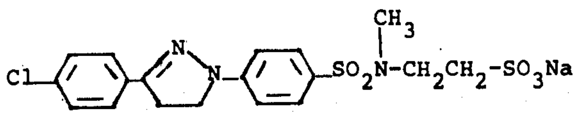

56. A compound of claim 53, wherein $R_4'$ signifies a hydrogen atom.

57. A compound of claim 54, and of formula

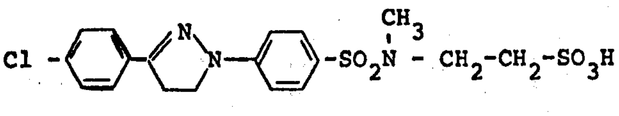

in free acid or salt form.

58. A compound of claim 54, and of formula

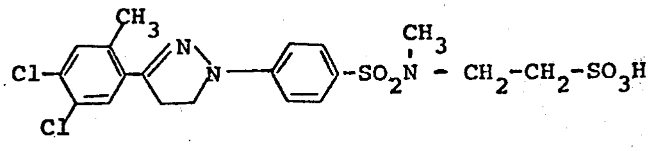
in free acid or salt form.
59. A compound of claim 53, and of formula
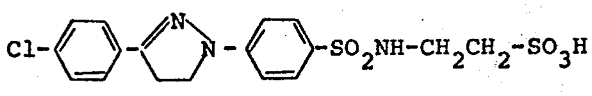
in free acid or salt form.
60. A compound of claim 56, and of formula
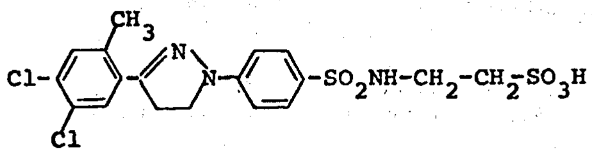
in free acid or salt form.
61. A compound of claim 38, and of formula
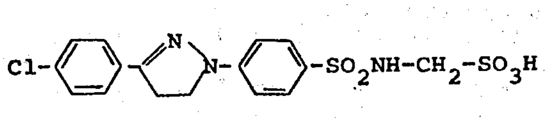
in free acid or salt form.
62. A compound of claim 38, and of formula
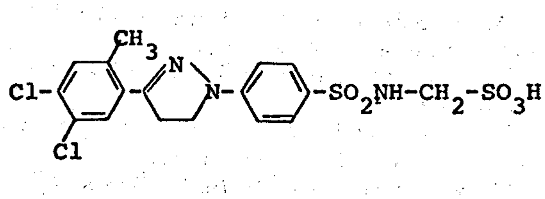
in free acid or salt form.
* * * * *